United States Patent
Lee et al.

(10) Patent No.: US 9,799,109 B2
(45) Date of Patent: Oct. 24, 2017

(54) RADIOGRAPHIC IMAGING APPARATUS AND CONTROL METHOD THEREOF

(71) Applicant: SAMSUNG ELECTRONICS CO., LTD., Suwon-si (KR)

(72) Inventors: Kang Eui Lee, Seoul (KR); Hyun Hwa Oh, Hwaseong-si (KR); Sung Su Kim, Yongin-si (KR); Young Hun Sung, Hwaseong-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 95 days.

(21) Appl. No.: 14/291,903

(22) Filed: May 30, 2014

(65) Prior Publication Data
US 2014/0355860 A1    Dec. 4, 2014

(30) Foreign Application Priority Data
May 30, 2013 (KR) .......................... 10-2013-0061520

(51) Int. Cl.
    *G06T 5/50* (2006.01)
    *A61B 6/00* (2006.01)

(52) U.S. Cl.
    CPC ............... *G06T 5/50* (2013.01); *A61B 6/463* (2013.01); *A61B 6/481* (2013.01); *A61B 6/482* (2013.01); *A61B 6/502* (2013.01); *A61B 6/5241* (2013.01); *G06T 2207/10016* (2013.01); *G06T 2207/10116* (2013.01); *G06T 2207/10152* (2013.01); *G06T 2207/20221* (2013.01); *G06T 2207/30068* (2013.01)

(58) Field of Classification Search
None
See application file for complete search history.

(56) References Cited

U.S. PATENT DOCUMENTS

| | | | | |
|---|---|---|---|---|
| 6,594,378 | B1 * | 7/2003 | Li | G06T 3/0068 128/922 |
| 7,298,383 | B2 * | 11/2007 | Vuylsteke | G06T 5/009 345/426 |
| 8,073,285 | B2 * | 12/2011 | Curtis | G06T 11/60 382/254 |

(Continued)

FOREIGN PATENT DOCUMENTS

| | | |
|---|---|---|
| JP | 2007-160094 A | 6/2007 |
| JP | 2012-81108 A | 4/2012 |

(Continued)

OTHER PUBLICATIONS

International Patent Application Publication No. WO 2012/015285, published Feb. 2, 2012.*

(Continued)

*Primary Examiner* — Matthew Bella
*Assistant Examiner* — Soo Shin
(74) *Attorney, Agent, or Firm* — Sughrue Mion, PLLC

(57) ABSTRACT

A radiographic imaging control method includes combining a plurality of images by applying a first weight to the plurality of images, displaying a composite image, acquired by combining the plurality of images, newly receiving a second weight with respect to the composite image, recombining the plurality of images based on the received second weight, and displaying a recombined image, acquired by recombining the plurality of images.

7 Claims, 16 Drawing Sheets

(56) References Cited

U.S. PATENT DOCUMENTS

| | | | |
|---|---|---|---|
| 2012/0039440 A1 | 2/2012 | Fan et al. | |
| 2013/0142412 A1* | 6/2013 | Oh .................... | A61B 6/4241 382/132 |
| 2013/0342577 A1* | 12/2013 | Wang .................... | G06T 11/60 345/634 |
| 2014/0133731 A1* | 5/2014 | Baumgart .............. | A61B 6/481 382/132 |
| 2015/0149565 A1* | 5/2015 | Ahmed ................ | H04L 65/403 709/206 |

FOREIGN PATENT DOCUMENTS

| KR | 10-2012-0011692 A | 2/2012 |
|---|---|---|
| KR | 10-2012-0028760 A | 3/2012 |

OTHER PUBLICATIONS

WO 2012/015285 A2.*
Farbspiel Photography, http://farbspiel-photo.com/learn/dynamic-before-and-after, attached version dated Jan. 15, 2013.*

* cited by examiner

CONTRAST ENHANCEMENT (1:0)

RADIOGRAPHIC IMAGING APPARATUS AND CONTROL METHOD THEREOF

CROSS-REFERENCE TO RELATED APPLICATION

This application claims priority from Korean Patent Application No. 10-2013-0061520, filed on May 30, 2013 in the Korean Intellectual Property Office, the disclosure of which is incorporated herein by reference in its entirety.

BACKGROUND

1. Field

Apparatuses and methods consistent with exemplary embodiments relate to a radiographic imaging apparatus and a control method thereof.

2. Description of the Related Art

A radiographic imaging apparatus emits radiation to an object, to acquire an image of the inside of the object.

The radiographic imaging apparatus uses properties in which, when radiation is emitted to an object, the radiation is absorbed and/or attenuated by the object according to characteristics of a material or a structure within the object. Specifically, when the radiation is emitted to an object, such as a human body, the radiation, which is not absorbed by the object, is transmitted through the object. The transmitted radiation is detected and converted into an electrical signal. Thereby, a radioactive signal is acquired and, thus, a radiographic image is generated.

Radiographic imaging apparatuses include, for example, a digital radiography (DR) apparatus, a fluoroscopy apparatus, a cardiography apparatus, an angiography apparatus, a computed tomography (CT) apparatus, and a mammography apparatus.

Since the radiographic imaging apparatus may easily detect the internal structure of an object, it may be used to detect lesions within a human body in medicine, or to detect the internal structure of an article or a machine part. Further, the radiographic imaging apparatus may be used to check the baggage in an airport, etc.

SUMMARY

One or more exemplary embodiments provide a radiographic imaging apparatus which may combine different radiographic images according to a user request and display a composite image suitable for the user request, and a control method thereof.

In accordance with an aspect of an exemplary embodiment, a radiographic imaging apparatus includes an image processor combining a plurality of images by applying at least one weight to each of the plurality of images, and a user interface displaying a composite image, acquired by combining the plurality of images, and newly receiving at least one weight to the composite image, wherein the image processor recombining the plurality of images by applying the new weight to the plurality of images.

The plurality of images may include a contrast enhanced image in which contrast of at least one basic image is enhanced, a tissue emphasized image in which tissues of the basic image are emphasized, or both the contrast enhanced image and the tissue emphasized image.

In accordance with an aspect of an exemplary embodiment, a control method of a radiographic imaging apparatus includes combining a plurality of images by applying at least one weight to each of the plurality of images, displaying a composite image, acquired by combining the plurality of images, newly receiving at least one weight to the composite image, recombining the plurality of images based on the received weight, and displaying a recombined image, acquired by recombining the plurality of images.

BRIEF DESCRIPTION OF THE DRAWINGS

The above and/or other aspects will be more apparent by describing certain exemplary embodiments with reference to the accompanying drawings, in which.

DETAILED DESCRIPTION

Figure 1:
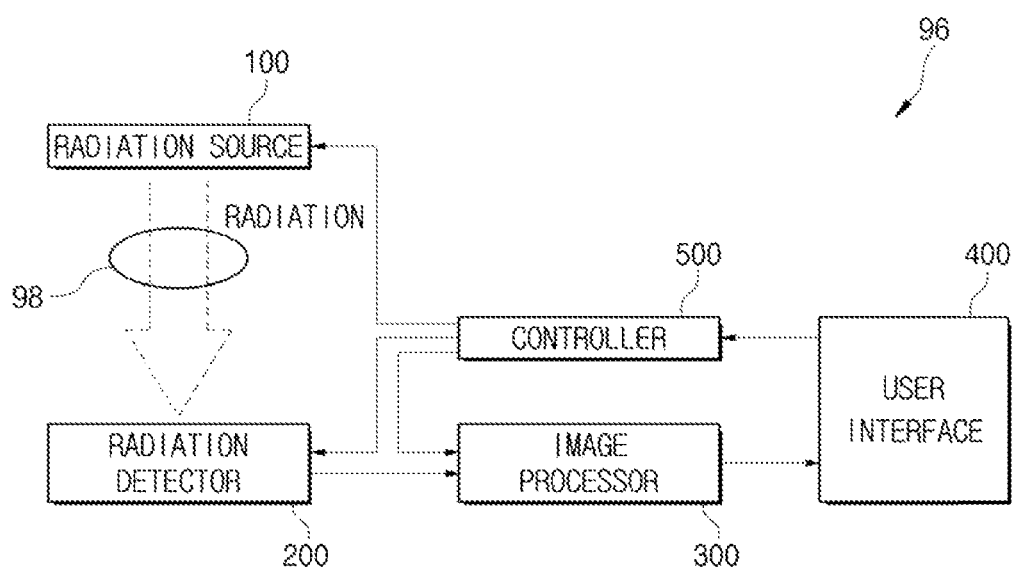
FIG. 1 is a view illustrating the configuration of a radiographic imaging apparatus in accordance with an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Hereinafter, a radiographic imaging apparatus in accordance with an exemplary embodiment will be described with reference to FIGS. 1 to 12.

Figure 2:
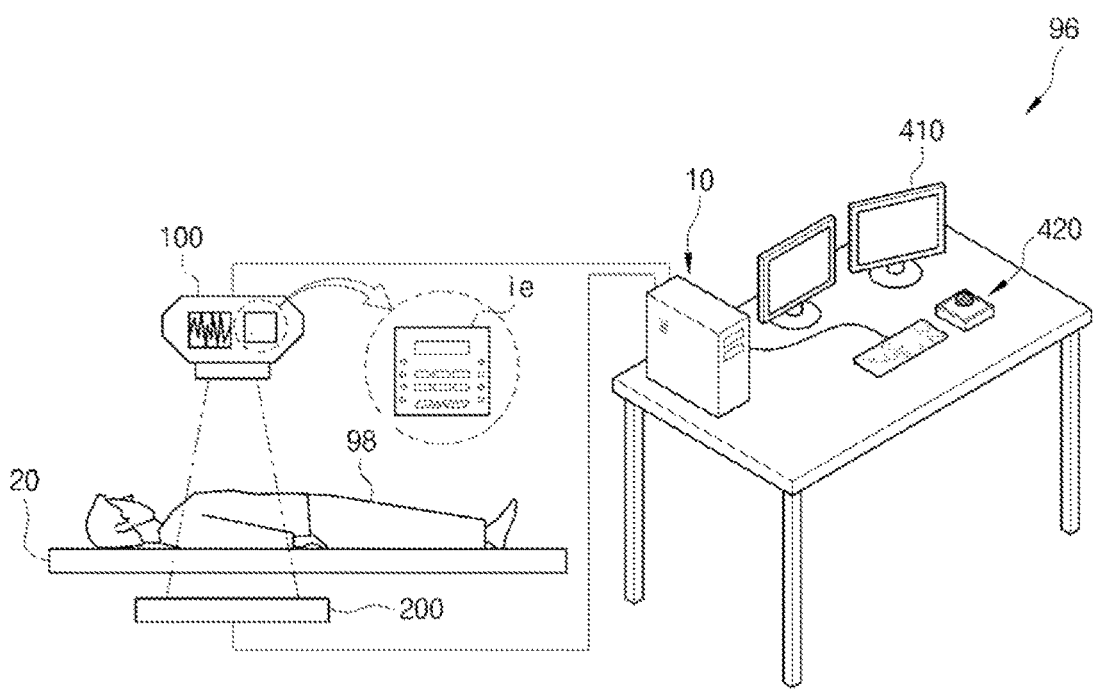
FIG. 2 is a view illustrating the radiographic imaging apparatus in accordance with an exemplary embodiment.

FIGS. 1 and 2 are views illustrating the radiographic imaging apparatus 96 in accordance with an exemplary embodiment.

As exemplarily shown in FIG. 1, the radiographic imaging apparatus in accordance with an exemplary embodiment includes a radiation source 100 applying radiation to an object 98, a radiation detector 200 receiving radiation transmitted by the object 98 or radiation directly reaching the radiation detector 200 and outputting a radioactive signal, an image processor 300 generating a radiographic image using the radioactive signal output from the radiation detector 200, a user interface 400 displaying the radiographic image or receiving instructions or command and various data, input by a user, and a controller 500 controlling the overall operation of the radiographic imaging apparatus.

More specifically, the radiographic imaging apparatus 96 may be a radiographic imaging apparatus to image the inside of a human body, as exemplarily shown in FIG. 2. The radiographic imaging apparatus may include a radiation source 100, a radiation detector 200, and a table 20 located between the radiation source 100 and the radiation detector 200 such that an object 98 is placed on the table 20. Here, the object 98 may be a human body.

Further, the radiographic imaging apparatus may include a console device 10 controlling the radiation source 100 and the radiation detector 200, receiving a radioactive signal transmitted from the radiation detector 200, and generating a radiographic image, and a user interface 400 providing the radiographic image or designated information to the user and receiving designated instructions or command or data, input by the user.

In accordance with an exemplary embodiment, the image processor 300 and the controller 500 of the above-described radiographic imaging apparatus may be provided in the console device 10.

According to exemplary embodiments, the user interface 400 may include an input unit 420 and an output unit 410 connected to the console device 10, as exemplarily shown in FIG. 2. Additionally or optionally, the user interface 400 may be an input/output module 102 provided on an outer housing of the radiation source 100, as exemplarily shown in FIG. 2.

Hereinafter, a radiographic imaging apparatus will be described. However, the described radiographic imaging apparatus is not limited to the radiographic imaging apparatus shown in FIG. 2.

For example, the radiographic imaging apparatus may be one of various kinds of radiographic imaging apparatuses, such as a radiographic imaging apparatus to image a whole human body, arms, legs, or teeth, a mammography apparatus to press breasts of a woman and image the pressed breasts, a fluoroscopy apparatus using fluoroscopy, a cardiography apparatus, an angiography apparatus using angiography, and a computed tomography (CT) apparatus to acquire image slices of an object by applying radiation to the object in a plurality of directions. Otherwise, the radiographic imaging apparatus may be a combination of two or more from among the above-described various kinds of radiographic imaging apparatuses. Such a radiographic imaging apparatus may be determined according to a kind of an object, a region of the object to be imaged, a purpose of imaging, or a kind of a generated radiographic image.

Hereinafter, the radiation source 100 of the radiographic imaging apparatus in accordance with an exemplary embodiment will be described.

Figure 3:
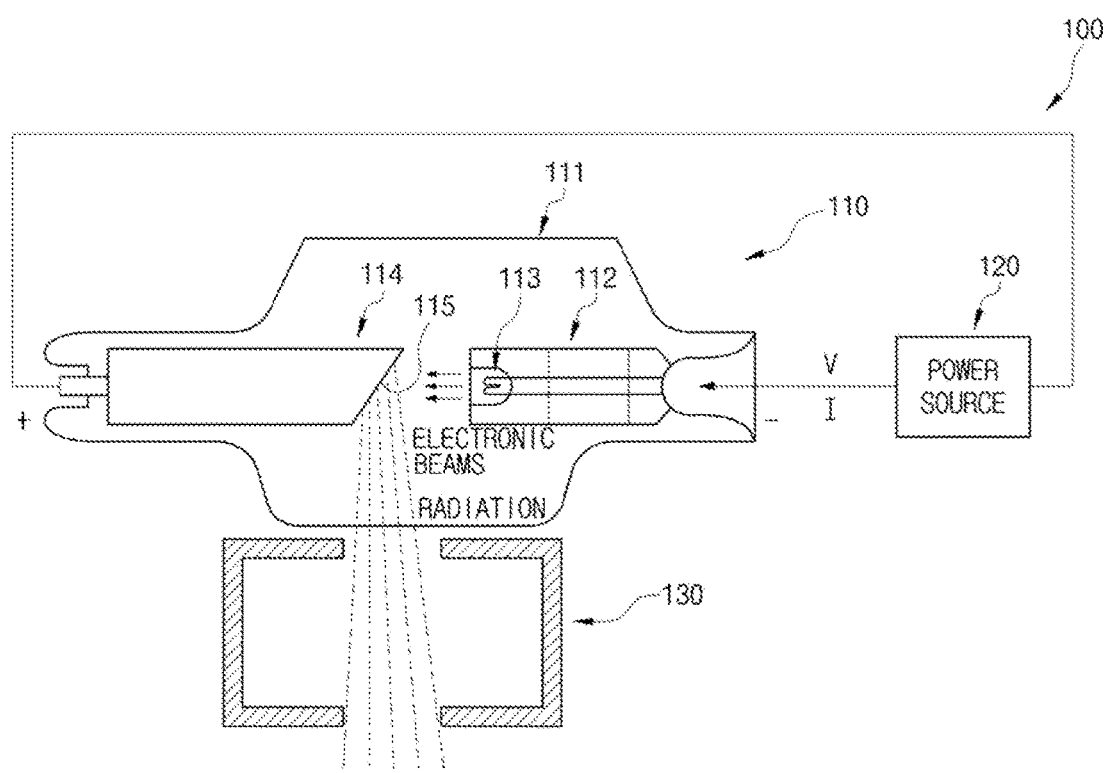
FIG. 3 is a view illustrating the configuration of a radiation source in accordance with an exemplary embodiment.

FIG. 3 is a view schematically illustrating the configuration of the radiation source in accordance with an exemplary embodiment.

The radiation source 100 of the radiographic imaging apparatus may generate radiation of designated energy and applies the generated radiation in a designated direction, for example, in a direction toward an object 98. Specifically, as exemplarily shown in FIG. 3, the radiation source 100 may include a radiation tube 110 generating radiation and a power source 120 applying voltage to the radiation tube 110.

The radiation tube 110 may include a tubular body 111 accommodating other parts, a cathode 112, and an anode 114, a filament 113 in which electrons are collected may be formed on the cathode 112, and a target 115 with which electrons generated from the filament 113 collide to be decelerated may be formed on the anode 114.

The tubular body 111 may be a glass tube formed of hard silicate glass, and maintain a high degree of vacuum of about 10-7 mmHg in the tubular body 111 while stably fixing the cathode 112 and the anode 114 within the tubular body 111.

The filament 113 of the cathode 112 is connected to the power source 120, is heated by tube voltage applied from the power source 120, and emits electrons of designated energy to the inside of the tubular body 111. The filament 113 of the cathode 112 may be formed of tungsten (W), in accordance with an exemplary embodiment. The cathode 112 may include a focusing electrode to focus the emitted electrons, as needed. Further, according to exemplary embodiments, the cathode 112 may use a carbon nanotube instead of the filament 113.

The electrons emitted from the filament 113 of the cathode 112 are accelerated within the tubular body 111 and move in the direction toward the anode 114. The accelerated electrons moving in the direction toward the anode 114 collide with the target 115 formed on the anode 114 and are rapidly decelerated by Coulomb's force. When the electrons are decelerated, radiation of energy corresponding to the applied tube voltage is generated based on the law of energy conservation.

The anode 114, in accordance with an exemplary embodiment, may be fixed, as exemplarily shown in FIG. 3. The fixed anode 114 may be cut at a designated angle, and the target 115 with which the electrons emitted from the filament 113 and accelerated collide may be formed at the cut region. The cut angle of the fixed anode 114 may be about 20 degrees from a tube axis in the vertical direction. A focus, i.e., a collision surface with which the accelerated electrons collide, may be formed on the target 115. The focus may have a rectangular shape. The focus may emit designated radiation according to collision of the accelerated electrons.

The anode 114 may be formed of metal, such as copper (Cu), and the target 115 may be formed of metal, such as tungsten (W), chrome (Cr), iron (Fe), and nickel (Ni).

Although not shown in the drawings, in accordance with an exemplary embodiment, the anode may have a rotatable disc shape. The anode may be rotated about moving direction of accelerated electrons as an axis. The anode may be rotated 3,600 to 10,800 times per minute. The boundary of the disc-shaped anode may be cut at a designated angle. A target with which electrons emitted from the filament 113 collide may be formed at the cut region of the boundary of the disc-shaped anode, in the same manner as the above-described embodiment. The anode may be rotated by a robot combined with the anode, and the target is also rotated according to rotation of the anode. When the target is rotated according to rotation of the anode, a heat accumulation rate may be increased and the size of the focus may be reduced, as compared to the fixed anode, and thus, a clearer radiographic image may be acquired.

When the anode 114 generates radiation, the generated radiation may be applied in a designated direction, for example, in the direction to the object 98. In this case, a designated collimator 130 may be formed in the irradiation direction.

The collimator 130 may transmit radiation progressing in a specific direction, and filter out radiation progressing in other directions than the specific direction through absorption or reflection. Thereby, the collimator 130 may cause the radiation source 100 to emit radiation within a designated range or in a designated direction. The collimator 130 may be formed of a material which may absorb radiation, for example, lead (Pb).

In accordance with exemplary embodiments, radiation having passed through the collimator 130 may pass through a designated filter. The designated filter may be formed of aluminum (Al) or copper (Cu), and attenuate the radiation having passed through the collimator 130 to a designated degree.

The power source 120 may adjust radiation energy released from the anode 114 by applying designated voltage, i.e., tube voltage, to the anode 114 and the cathode 112 of the radiation tube 110.

The radiation source 100 may control the energy and intensity of radiation according to tube voltage applied from the power source 120 to the radiation tube 110, tube current, and radiation exposure time.

Figure 4A:
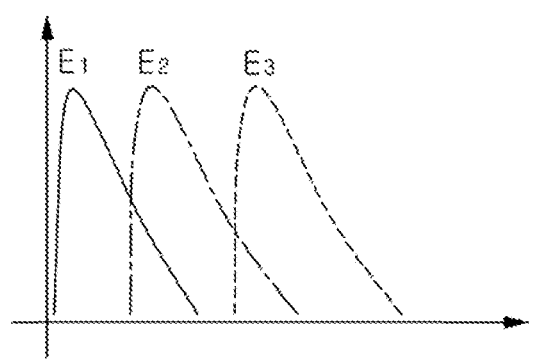
FIGS. 4A and 4B are graphs illustrating various kinds of irradiations.
Figure 4B:
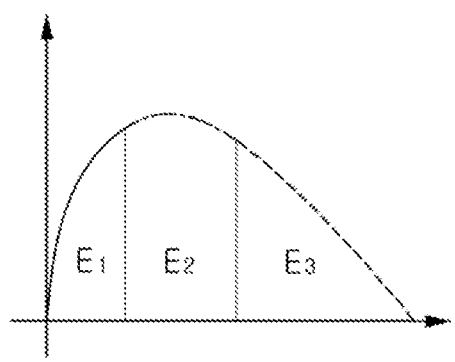

FIGS. 4A and 4B are graphs illustrating irradiation.

The radiation source 100 may generate radiation of a plurality of different energy bands and irradiate an object 98 with the radiation, as exemplarily shown in FIG. 4A. The radiation source 100 may apply radiation of different energy bands to the object 98 by applying different tube voltages to the radiation tube 110 plural times. According to emission of radiation of different energy bands by the radiation source 100, at least two radiographic images may be generated.

Respective tissues within the object 98 absorb some of the applied radiation and transmit some of the applied radiation. The radiation detector 200 may receive the transmitted radiation. The respective tissues within the object 98 have different degrees of absorbing or transmitting radiation according to characteristics of the tissues. An attenuation coefficient numerically expresses a degree of absorbing or transmitting radiation by each of the respective tissues within the object 98.

Specifically, an intensity of radiation to generate a radiographic image in the radiographic imaging apparatus is given according to Equation 1 below.

$$I = I_0 e^{-\mu t}$$ [Equation 1]

Here, $I_0$ is the intensity of emitted radiation which may reach the radiation detector 200 if an object 98 is not present;

I is the intensity of radiation transmitted by the object 98, i.e., the intensity of radiation which is partially absorbed by the object 98 while passing through the object 98 and is thus attenuated;

μ is an attenuation coefficient of an internal tissue of the object 98; and t is the thickness of the internal tissue of the object 98 through which the radiation has been transmitted.

As stated in Equation 1, it may be understood, as the thickness of the internal tissue or the attenuation coefficient of the object 98 increases, a larger amount of radiation is attenuated.

The attenuation coefficient may vary according to energy bands of radiation.

Figure 5:
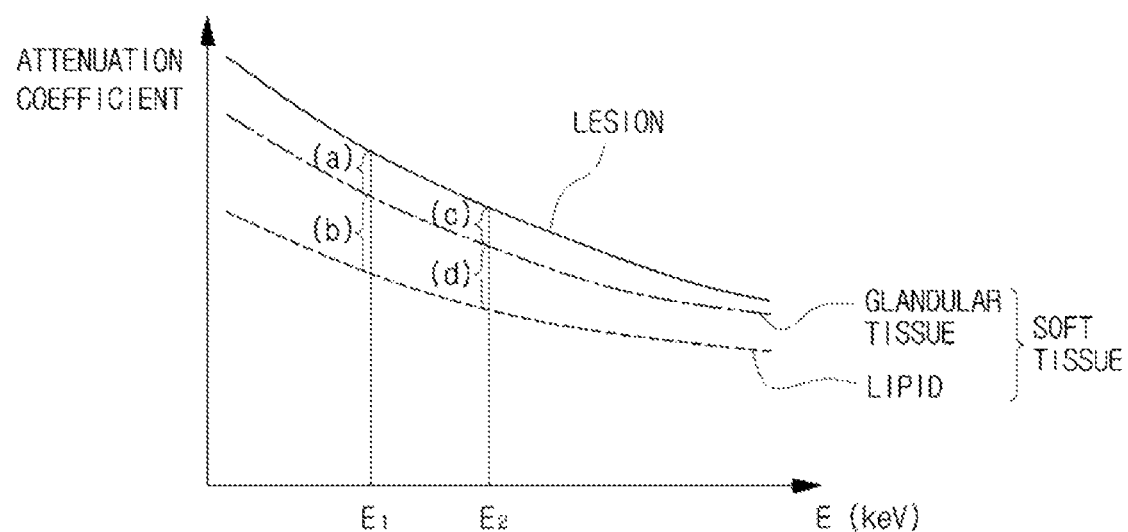
FIG. 5 is a graph representing attenuation coefficients.

FIG. 5 is a graph representing attenuation coefficients of various tissues in a human body.

With reference to FIG. 5, it may be understood that attenuation coefficients of tissues within an object 98, for example, glandular tissues and lipids among soft tissues, are different at the same energy, for example, at first energy (E1) (in region (b) of FIG. 5). Further, it may be understood that attenuation coefficients of hard tissues, such as lesions, and glandular tissues are also different at the same energy, for example, at first energy (E1) (in region (a) of FIG. 5). Various tissues or structures within the object 98 may be classified according to differences of attenuation coefficients among lesions and respective tissues, thus being imaged.

Further, with reference to FIG. 5, it may be understood that the attenuation coefficient of tissues within the object 98, for example, glandular tissues among soft tissues, is gradually decreased as the energy band of radiation increases, and the attenuation coefficient of other tissues within the object 98, for example, lipids, is also gradually decreased as the energy band of radiation increases. In this case, differences of attenuation coefficients according to irradiation at different energy bands, for example, the first energy band (E1) and the second energy band (E2), may be different.

That is, tissues or configurations within the object 98 may have different degrees of absorbing or transmitting radiation according to energy bands of emitted radiation. Therefore, when the same object 98 is irradiated with radiation of different energy bands, for example, the first energy band (E1) and the second energy band (E2), radiographic images of a plurality of different energy bands may be acquired. The radiographic images of the plural energy bands exhibit absorption characteristics of the respective energy bands.

The radiation source 100 may irradiate an object 98 with radiation having a wide band energy spectrum, as exemplarily shown in FIG. 4B. In this case, radiographic images of a plurality of energy bands (E1 to E3) may be acquired by dividing the wide band energy into the plurality of energy bands (E1 to E3) using the radiation detector 200.

Radiation emitted from the radiation source 100 and transmitted through the object 98 may be detected by the radiation detector 200, as exemplarily shown in FIGS. 1 and 2.

Hereinafter, the radiation detector will be described.

The radiation detector 200 may receive radiation emitted from the radiation source 100, and convert the received radiation into a radioactive signal.

Specifically, the radiation detector 200 may acquire the radioactive signal by converting the received radiation directly into an electrical signal in accordance with an exemplary embodiment, or acquire the radioactive signal by converting the received radioactive signal into visible rays and converting the visible rays into an electrical signal in accordance with an exemplary embodiment.

Figure 6:
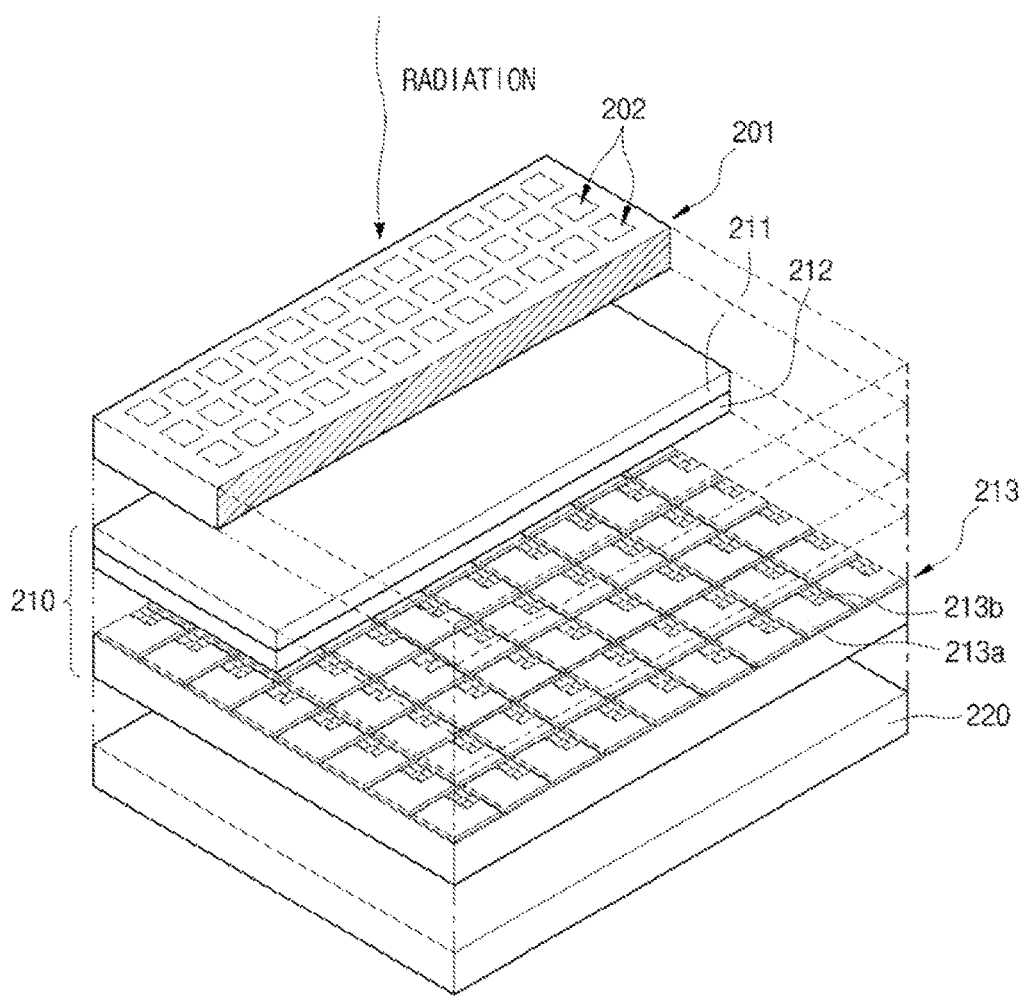
FIG. 6 is a perspective view of a radiation detector in accordance with an exemplary embodiment.

FIG. 6 is a perspective view of the radiation detector in accordance with an exemplary embodiment.

As exemplarily shown in FIG. 6, the radiation detector 200 may include a collimator 201 and a radiation detection panel 210. A substrate 220 may be formed on the rear surface of the radiation detection panel 210.

If radiation emitted from the radiation source 100 is transmitted through the internal regions of the object 98, the radiation is refracted or scattered according to features, characteristics, or structures of tissues within the object 98. Based on such refraction or scattering of radiation, under ideal conditions, the radiation detection panel 210 of the radiation detector 200 does not receive radiation transmitted by the tissues at a designated position but may receive radiation transmitted by the tissues at a different position and, thereby, precision of radiographic images may be lowered.

The collimator 201 may filter out refracted or scattered radiation so that among radiation transmitted by the object 98, only radiation in a specific direction may reach the radiation detection panel 210, thus allowing radiation having passed through designated tissues to reach a proper point, i.e., pixel, of the radiation detection panel 210. The collimator 201 may include a plurality of diaphragms formed of a material absorbing radiation, such as lead (Pb), as exemplarily shown in FIG. 6. The plural diaphragms may absorb scattered or refracted radiation so that the scattered or refracted radiation does not reach the radiation detection panel 210.

The radiation detection panel 210 may include a first electrode 211, a flat plate 213 on which at least one second electrode (pixel electrode) 213a is arranged, and a semiconductor material layer 212 arranged between the first electrode 211 and the flat plate 213.

The first electrode 211 may have positive (+) or negative (−) polarity. The second electrode 213a may have positive (+) or negative (−) polarity according to polarity of the first electrode 211. Designated bias voltage may be applied between the first electrode 211 and the second electrode 213a.

The semiconductor material layer 212 may generate electron-hole pairs according to incidence and absorption of radiation. The generated electron-hole pairs move to the second electrode 213a based on polarity of the first electrode 211 and the second electrode 213a. In this case, light spreading does not occur. In accordance with an exemplary embodiment, the semiconductor material layer 212 may be formed of a photoconductor, particularly, amorphous selenium.

The flat plate 213 may include the second electrode 213a to which the generated electrons or holes are transmitted, and at least one thin film transistor 213b. The flat plate 213 may consist of at least one CMOS chip, in accordance with exemplary embodiments. One second chip 213a and one thin film transistor 213b may be installed on each CMOS chip.

The second electrode 213a may receive holes or negative charges transmitted from the semiconductor material layer 212 according to polarities of the first electrode 211 and the second electrode 213a. The holes or negative charges transmitted to the second electrode 213a may be stored in a designated storage element, for example, a capacitor. With reference to FIG. 6, at least one second electrode 213a may be arranged in at least one array on the flat plate 213. For example, the respective second electrodes 213a may be arranged in a one-dimensional (1D) array on the flat plate 213, or be arranged in a two-dimensional (2D) array on the flat plate 213, as exemplarily shown in FIG. 6.

The thin film transistor 213b may read an electrical signal transmitted from the second electrode 213a or stored in the designated storage element. As exemplarily shown in FIG. 6, corresponding thin film transistors 213b may be connected to the respective second electrodes 213a.

Although not shown in the drawing, in accordance with exemplary embodiments, a phosphor screen may be disposed between the collimator 201 and the radiation detection panel 210. The phosphor screen may receive radiation emitted from the radiation source 100 and output designated light. In this case, at least one photodiode may be installed on the above-described flat plate 213. The respective photodiodes may be arranged in a 1D array or be arranged in a 2D array, in the same manner as the second electrodes 213a.

The substrate 220 attached to the rear surface of the radiation detection panel 10 may control reading of an electrical signal detected by the radiation detection panel 210. Further, the substrate 220 may stably fix the radiation detection panel 210.

Further, although not shown in the drawings, the radiation detection panel 210 may include a scintillator receiving radiation and outputting designated photons, for example, visible photons, according to the received radiation. The radiation detection panel 210 may further include a light sensing element to sense the visible photons output from the scintillator, for example, a photodiode. The photodiode may output a designated electrical signal, for example, an electric charge packet including holes or negative charges, according to the visible photons. The output electric charge packet may be stored in a designated storage element, for example, a capacitor.

In accordance with an exemplary embodiment, the radiation detector 200 may be a photon counting detector (PCD). The PCD may count the number of photons more than critical energy from a radioactive signal and thus, acquire designated data required to generate radiographic images. The PCD may include an amplifier, a comparator, and a counter. The amplifier, the comparator, and the counter may be implemented by a designated circuit formed on a designated substrate.

The amplifier may amplify an input radioactive signal by charging a designated charging element, for example, a capacitor, with the radioactive signal.

The comparator may judge whether or not the electrical signal amplified by the amplifier is greater than critical energy through comparison, and output a comparison result signal. The comparison result signal may be a binary signal. For example, if the amplified electrical signal is greater than the critical energy, the comparison result signal may be 1, and on the other hand, if the amplified electrical signal is less than the critical energy, the comparison result signal may be 0. The energy spectrum of radiation may be divided, as exemplarily shown in FIG. 4B, by adjusting the critical energy with which the electrical signal is compared.

The counter may count the number of photons greater than the critical energy using the comparison result signal transmitted from the comparator and output photon counting result information. The photon counting result information may be intensity of radiation.

Radioactive signals acquired by such a method may be read by the image processor 300, and the image processor 300 may generate at least one radiographic image using the read radioactive signals.

Hereinafter, the image processor will be described.

Figure 7:
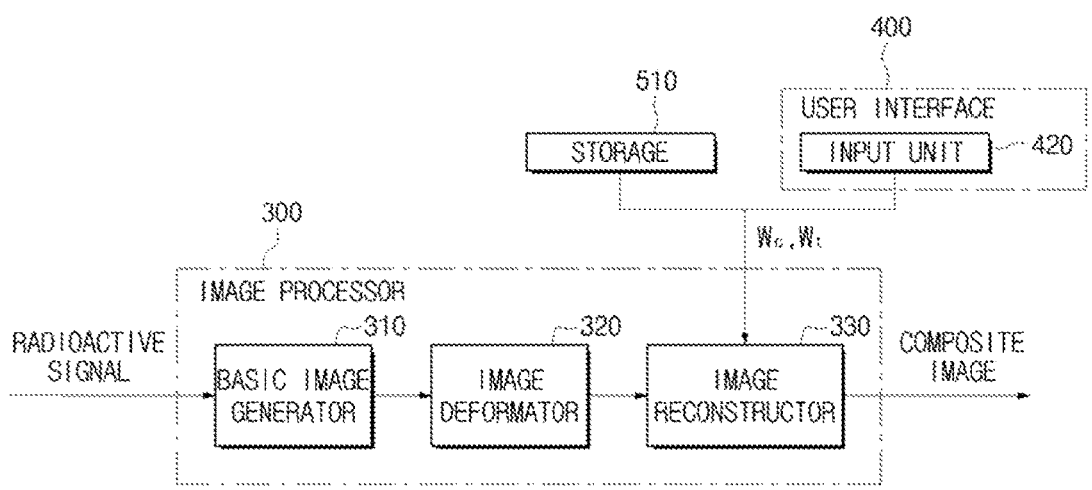
FIG. 7 is a block diagram of an image processor in accordance with an exemplary embodiment.

FIG. 7 is a block diagram of the image processor in accordance with an exemplary embodiment.

As exemplarily shown in FIG. 7, the image processor 300 may include a basic image generator 310, an image deformator 320, and an image reconstructor 330.

The basic image generator 310 may generate at least one radiographic image based on a read radioactive signal. In accordance with an exemplary embodiment, the basic image generator 310 may generate a plurality of radiographic images corresponding to a plurality of different radioactive energy bands. The radiographic images generated by the basic image generator 310 may be used as basic images for deformed images generated by the image deformator 320.

The image deformator 320 may generate a plurality of deformed images by deforming the basic images generated by the basic image generator 310. For example, the image deformator 320 may generate a plurality of deformed images in which a specific region is emphasized or contrast is enhanced by giving designated weights to the images and then combining the images.

The image reconstructor 330 may generate a designated composite image by combining the plural deformed images generated by the image deformator 320. The image reconstructor 330 may generate a designated composite image by applying designated weights wC and wT transmitted from the outside to the deformed images. The designated weights wC and wT transmitted from the outside may be stored in the storage 510, or may be input by a user through the user interface 400, for example, the input unit 420 of the user interface 400.

Figure 8:
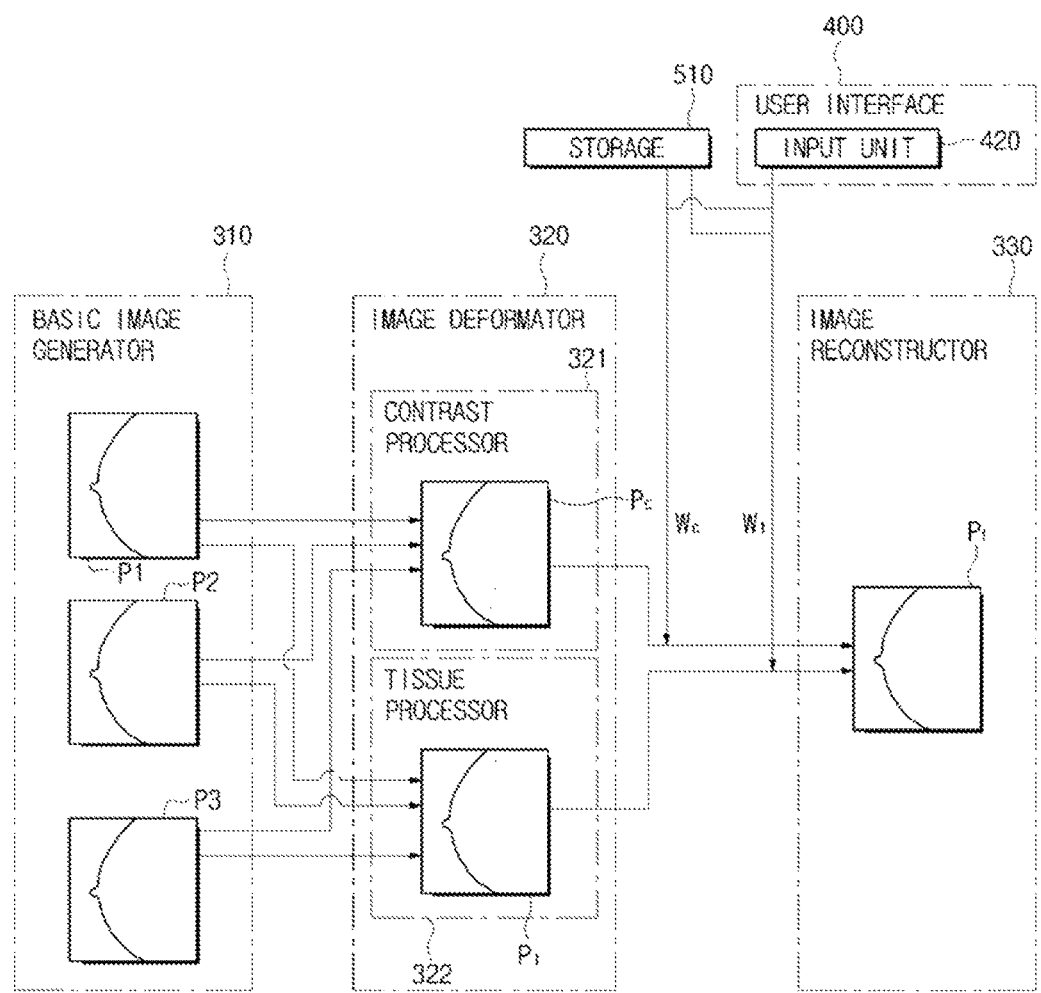
FIG. 8 is a view illustrating operation of the image processor in accordance with an exemplary embodiment.

FIG. 8 is a view illustrating operation of the image processor in accordance with an exemplary embodiment.

If the radiation source 100 irradiates an object 98 with radiation of a plurality of different energy bands E1 to E3, as described above, the basic image generator 310 may generate a plurality of radiographic images p1, p2, and p3 corresponding to the plurality of different energy bands E1 to E3. Since attenuation coefficients of materials within the object 98 are different according to energy bands of radiation, as described above with reference to FIG. 5, the respective radiographic images p1 to p3 may be different.

The image deformator 320 may generate a plurality of different deformed images, for example, a contrast enhanced image $p_C$ and a tissue emphasized image $p_T$, using the plurality of radiographic images p1 to p3.

In accordance with an exemplary embodiment, the image deformator 320 may include a contrast processor 321 performing contrast enhancement (CE) on at least one of the radiographic images p1 to p3 of the plural energy bands E1 to E3. Contrast enhancement (CE) may be performed on all or some of the radiographic images p1 to p3 or on some of the radiographic images p1 to p3, and a new radiographic image $p_C$ in which contrast is enhanced may be generated using all of the radiographic images p1 to p3 of the plural energy bands E1 to E3, as needed. The contrast processor 321 may perform contrast enhancement (CE) of the radiographic images p1 to p3 using a known contrast enhancement method of related art image processing.

Further, in accordance with an exemplary embodiment, the image deformator 320 may include a tissue processor 322 generating a tissue emphasized image $p_T$ by emphasizing designated tissues within the images using the plural radiographic images p1 to p3. The tissue processor 322 may generate the tissue emphasized image $p_T$ by emphasizing specific tissues in the radiographic images or by removing or reducing non-interested tissues other than the specific tissues. For example, the tissue processor 322 may acquire the tissue emphasized image $p_T$ in which specific tissues are emphasized using differences of attenuation coefficients among radiation of different energy bands. More specifically, when the tissue processor 322 acquires the attenuation coefficient of a material to be removed among designated materials within the object 98, determines weights to the plural images p1 to p3 acquired through radiation of different energy bands according to an attenuation coefficient ratio, and performs weighted subtraction of the plural images p1 to p3, a radiographic image from which the material is removed may be acquired. In this case, other materials than the material to be removed have attenuation coefficients different from that of the material to be removed at the respective energy bands and reduction rates of the attenuation coefficients of these materials according to increase of energy are different from that of the material to be removed, these materials remain in an image acquired through weighted subtraction of the plural images p1 to p3. For example, in case of breast tissues, a tissue emphasized image $p_T$ in which tissues other than adipose tissues, for example, lesions, such as cancer tissues, are emphasized by removing a large amount of adipose tissues distributed in the breast tissues.

When the image deformator 320 outputs a plurality of different images, for examples, the contrast enhanced image $p_C$ and the tissue emphasized image $p_T$, the image reconstructor 330 may generate a composite image $p_f$ by combining the plurality of different images, for example, the contrast enhanced image $p_C$ and the tissue emphasized image $p_T$, and the output the composite image $p_f$ to the outside.

The image reconstructor 330 may generate a designated composite image $p_f$ by calculating a weighted sum by applying corresponding weights, for example of a contrast enhanced image weight $w_C$ and a tissue emphasized image weight $w_T$, to the above-described respective images, for example, the contrast enhanced image $p_C$ and the tissue emphasized image $p_T$.

The respective weights, for example, the contrast enhanced image weight $w_C$ and the tissue emphasized image weight $w_T$, may be determined by the different weights, for example, the tissue emphasized image weight $w_T$ and the contrast enhanced image weight $w_C$. That is, when the contrast enhanced image weight $w_C$ is determined, the tissue emphasized image weight $w_T$ may be determined by the determined contrast enhanced image weight $w_C$. The opposite may be achieved in the same manner.

The image reconstructor 330 may determine ratios of the respective images to be combined using weights to be applied to the respective images to be combined. For example, the image reconstructor 330 may determine which one of the respective images, for example, the contrast enhanced image weight $w_C$ and the tissue emphasized image weight $w_T$, is more emphasized according to the weights. The sum of the weights applied to the respective images may be 1. That is, if a weight applied to one image, for example, the contrast enhanced image weight $w_C$ applied to the contrast enhanced image $p_C$, is 0.5, a weight applied to the other image, for example, the tissue emphasized image weight $w_T$ applied to the tissue emphasized image $p_T$, may be 0.5. If weights applied to the respective images, for example, the contrast enhanced image weight $w_C$ and the tissue emphasized image weight $w_T$, are 0.5, the respective images, for example, the contrast enhanced image $p_C$ and the tissue emphasized image $p_T$, may be combined at the same ratios.

In accordance with an exemplary embodiment, the image reconstructor 330 may use at least one initial weight stored in the storage 510 as the weight applied to each of the plural images. The composite image $p_f$ acquired using the initial weight may be displayed to a user through the user interface 400. When the user inputs at least one new weight through the user interface 400 after the composite image $p_f$ has been output and displayed to the user, the image reconstructor 330 may recombine the plural images, for example, the contrast enhanced image $p_C$ and the tissue emphasized image $p_T$, using the new input weight using the user interface 400.

That is, the image reconstructor 330 may combine the plural images, for example, the contrast enhanced image $p_C$ and the tissue emphasized image $p_T$, using a plurality of initial weights, for example, an initial weight of the contrast enhanced image weight $w_C$ and an initial weight of the tissue emphasized image weight $w_T$, and, when a plurality of new weights, for example, a new weight of the contrast enhanced image weight $w_C$ and a new weight of the tissue emphasized image weight $w_T$, is input by the user through the input unit 420 of the user interface 400, recombine the plural images, for example, the contrast enhanced image $p_C$ and the tissue emphasized image $p_T$, using the plurality of new input weights. The recombined image $p_f$ acquired using the new input weights may be also output to the outside and displayed to the user.

Both the output composite image and recombined image may be displayed to the user through the user interface 400.

Hereinafter, the user interface will be described.

Figure 9:
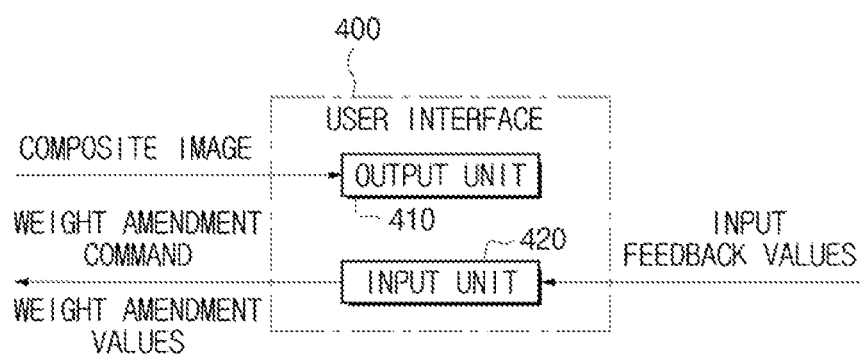
FIG. 9 is a block diagram of user interface in accordance with an exemplary embodiment.
Figure 10:
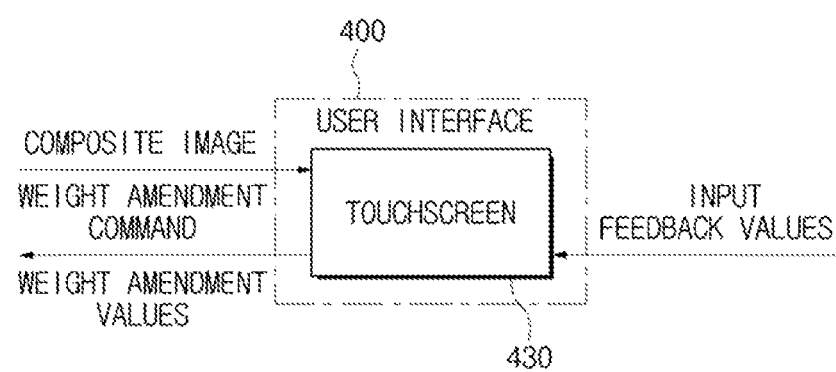
FIG. 10 is a block diagram of user interface in accordance with an exemplary embodiment.

FIGS. 9 and 10 are block diagrams of user interfaces in accordance with an exemplary embodiment.

As exemplarily shown in FIG. 9, the user interface 400 may include an output unit 410 outputting a composite image and an input unit 420 receiving feedback values from a user.

The output unit 410 may receive a composite radiographic image or a recombined radiographic image from the image reconstructor 330, and display the received composite radiographic image or recombined radiographic image to the user.

The output unit 410 may display the basic images p1 to p3 or the deformed images, for example, the contrast enhanced image $p_C$ and the tissue emphasized image $p_T$. In accordance with an exemplary embodiment, the output unit 410 may include various display devices, such as a monitor device, connected to the designated console device 10 through wired and wireless communication networks, as shown in FIG. 2.

The input unit 420 may receive designated information, instructions or command, input by an operator of the radiographic imaging apparatus, for example, a doctor, a radiologist, a nurse, or a patient. Specifically, the input unit 420 receives various pieces of information, instructions, or command regarding radiography or radiographic image processing, for example, a frequency of irradiation or a radiation dose, and transmits the received various pieces of information, instructions, or command to the controller 500.

Further, after the output unit 410 displays a composite image using initial weights, the input unit 420 may receive feedback values for the composite image, input by the user. The feedback values input by the user may be new weights to generate a recombined image through the image reconstructor 330. The input unit 420 may output a weight amendment command or weight amendment values according to the feedback values input by the user and transmit the weight amendment command or the weight amendment values to the image reconstructor 330. The input unit 420 may transmit the weight amendment command or the weight amendment values to the image reconstructor 330 with the help of a separate processor.

In accordance with an exemplary embodiment, the input unit 420 may include various user interfaces directly installed on the radiographic imaging apparatus, for example, various buttons, a keyboard, a mouse, a track-ball, a track-pad, various levers, a handle, and a stick, or a combination of at least two thereof.

The input unit 420 may be directly installed on some modules of the radiographic imaging apparatus, for example, on the radiation source 100, as exemplarily shown in FIG. 2, or be provided in the separate console device 10 which is connected to the radiographic imaging apparatus through a wired and/or wireless communication network and may transmit and receive data to and from the radiographic imaging apparatus.

In accordance with an exemplary embodiment, the user interface 10 may include a touchscreen 430 which may perform display of images and input of instructions or command, as exemplarily shown in FIG. 10.

The touchscreen 430 is an input/output device which senses user touch on a display screen displaying designated images and receives designated instructions or command input according to the sensed touch. The touchscreen 430 may sense a user finger or a stylus pen contacting the screen or moving while contacting the screen, generate a designated electrical signal according to a sensed result, and transmit the generated electrical signal to a separate processor. The touchscreen 430 may use various kinds of touchscreens, such as a resistive touchscreen sensing external pressure, a capacitive touchscreen using static electricity in a human body, an infrared touchscreen sensing a touched position using infrared light, and an ultrasonic touchscreen sensing a touched position using ultrasonic waves, according to implementation principles and operation methods of sensing touch.

The touchscreen 430 may display a composite image transmitted from the image reconstructor 330 to a user and receive feedback values of image composition, input by the user, as exemplarily shown in FIG. 10. The feedback values input by the user may be new weights to generate a recombined image through the image reconstructor 330. In the same manner as in the embodiment shown in FIG. 9, the touchscreen 430 may output a weight amendment command or weight amendment values according to the feedback values input by the user and transmit the weight amendment command or the weight amendment values to the image reconstructor 330.

FIGS. 11A to 11C and 12 are views illustrating display images on a screen in accordance with an exemplary embodiment.

FIGS. 11A to 11C and 12 illustrate display images displayed on the screen of the above-described output unit 410 or touchscreen 430 of the user interface 400.

With reference to FIGS. 11A to 11C and 12, various images, such as a composite image and a recombined image, acquired by the image reconstructor 330, and deformed images acquired by the image deformator 320 may be displayed in a partial zone 413 of a screen 412, and designated weights applied to the composite image $p_f$ may be displayed in another partial zone of the screen 412 where the various images are not displayed.

In order to display the designated weights used in combination of images, a designated graphical user interface (GUI) may be displayed in another partial zone 450 of the screen 412. In accordance with an exemplary embodiment, a user may confirm weights applied to the current composite image through the GUI, and change weights necessary to combine images by inputting new weights using the GUI as needed.

Figure 11A:
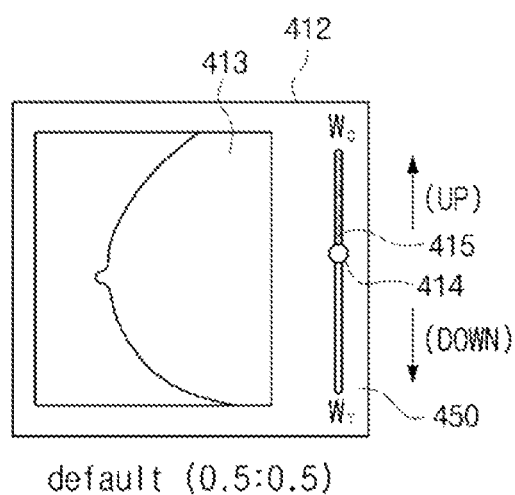
FIGS. 11A, 11B, and 11C are views illustrating display images on a screen in accordance with an exemplary embodiment.
Figure 11B:
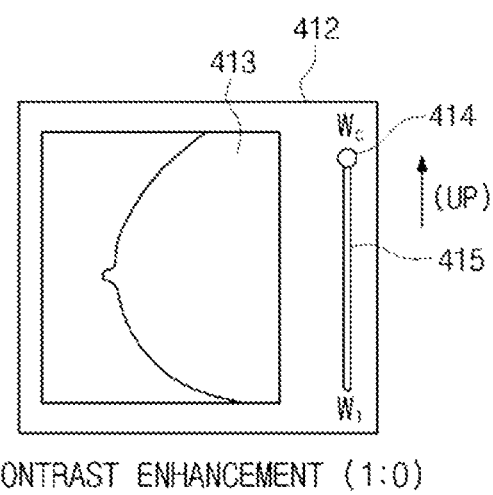
Figure 11C:
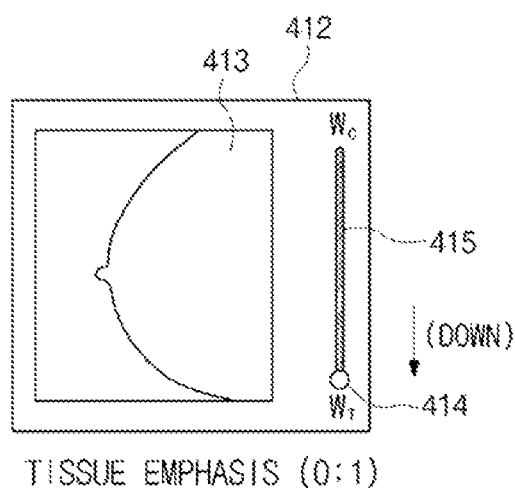

In accordance with an exemplary embodiment, the GUI may have the shape of an adjustment bar including a designated display mark 414 and a track displaying a scale on which the display mark 414 is movable, as exemplarily shown in FIGS. 11A to 11C.

The display mark 414 may display weights, for example, the contrast enhanced image weight $w_C$ and the tissue emphasized image weight $w_T$, applied to the respective images to be combined, for example, the contrast enhanced image $p_C$ and the tissue emphasized image $p_T$, according to positions on the track 415.

For example, as exemplarily shown in FIG. 11A, if the display mark 414 is located at the center of the track 415, this may mean that the weights applied to the respective images are 0.5. For example, this may mean that the contrast enhanced image weight $w_C$ and the tissue emphasized image weight $w_T$, applied to the images to be combined are equal.

As exemplarily shown in FIG. 11B, if the display mark 414 is located at the upper end of the track 415, this may mean that the weights applied to the respective images are 1 and 0. For example, this may mean that only the contrast enhanced image weight $w_C$ is used in combination of the images. In this case, only the contrast enhanced image $p_C$ may be displayed in the partial area 413 of the screen.

As exemplarily shown in FIG. 11C, if the display mark 414 is located at the lower end of the track 415, this may mean that the weights applied to the respective images are 0 and 1. For example, this may mean that only the tissue emphasized image weight $w_T$ is used in combination of the images. In this case, only the tissue emphasized image $p_T$ may be displayed in the partial area 413 of the screen.

The user may determine weights to be applied to the respective images, for example, the contrast enhanced image weight $w_C$ to be applied to the contrast enhanced image $p_C$ and the tissue emphasized image weight $w_T$ to be applied to the tissue emphasized image $p_T$, by moving the display mark 414 by operating the input unit 420 or performing touch on the touchscreen 430.

For example, the user may determine on which one of the respective images, for example, the contrast enhanced image $p_C$ and the tissue emphasized image $p_T$, higher weight is placed through movement of the display mark 414. More specifically, the user may generate a designated composite image $p_f$ in which the ratio of the contrast enhanced image $p_C$ is increased and the ratio of the tissue emphasized image $p_T$ is decreased by increasing the contrast enhanced image weight $w_C$ and decreasing the tissue emphasized image weight $w_T$ by moving the display mark 414 in the upward direction, as exemplarily shown in FIG. 11B. Further, the user may generate a designated composite image $p_f$ in which the ratio of the contrast enhanced image $p_C$ is decreased and the ratio of the tissue emphasized image $p_T$ is increased by decreasing the contrast enhanced image weight $w_C$ and increasing the tissue emphasized image weight $w_T$ by moving the display mark 414 in the downward direction, as exemplarily shown in FIG. 11C.

Figure 12:
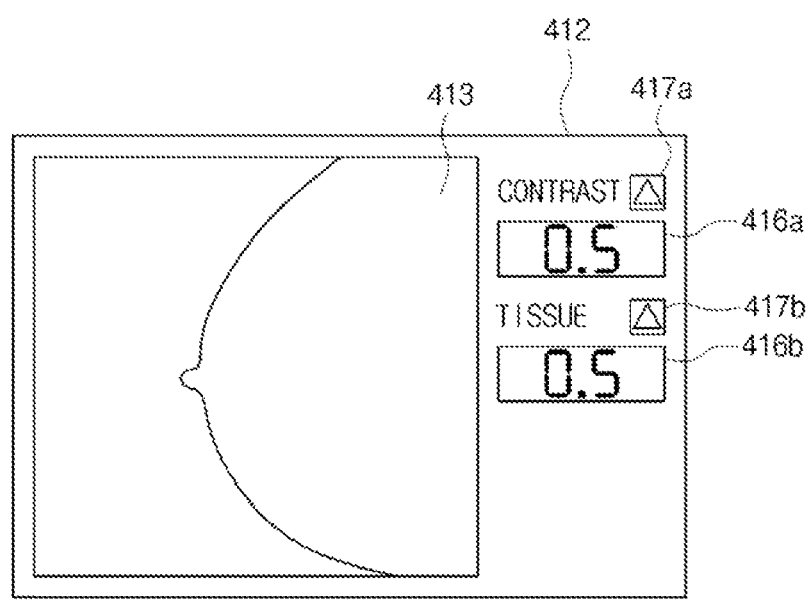
FIG. 12 is a view illustrating display image on a screen in accordance with an exemplary embodiment.

Further, the GUI may include numeric displays 416a and 416b displaying designated digital numbers, as exemplarily shown in FIG. 12. The numeric displays 416a and 416b may display weights to be applied to the respective images, for example, the contrast enhanced image weight $w_C$ to be applied to the contrast enhanced image $p_C$ and the tissue emphasized image weight $w_T$ to be applied to the tissue emphasized image $p_T$. The user may amend the weights displayed on the numeric displays 416a and 416b by operating the input unit 420 or performing touch on the touchscreen 430. If the user interface 400 includes the touchscreen 430, input areas 417a and 417b to amend the respective weights may be further displayed at designated positions of the screen 413. The user may amend the weights by performing touch through a method of pressing the input areas 417a and 417b. The amended weights may be displayed in the input areas 417a and 417b in real time or after a designated time has elapsed.

Although FIGS. 11A to 11C and FIG. 12 illustrate the GUI at the right region of the screen 412, the GUI may be displaced at the upper, left, or lower region of the screen 412 or be disposed at the center of the screen 412. Further, although FIGS. 11A to 11C illustrate the case in which, if the display mark 414 is moved in the upward direction, the contrast enhanced image weight $w_C$ is more increased, and if the display mark 414 is moved in the downward direction, the tissue emphasized image weight $w_T$ is more increased, the kind or size of a weight which is amended according to movement of the display mark 414 may be arbitrarily set by those in the art.

Further, the GUI may have various shapes which may display designated information to receive feedback values of weights from a user and receive designated weights as needed, in addition to the shapes shown in FIGS. 11A to 11C and FIG. 12. The display position, display method, or display shape of the GUI may be arbitrarily set by those skilled in the art.

Hereinafter, a control method of a radiographic imaging apparatus in accordance with an exemplary embodiment will be described with reference to FIG. 13.

Figure 13:
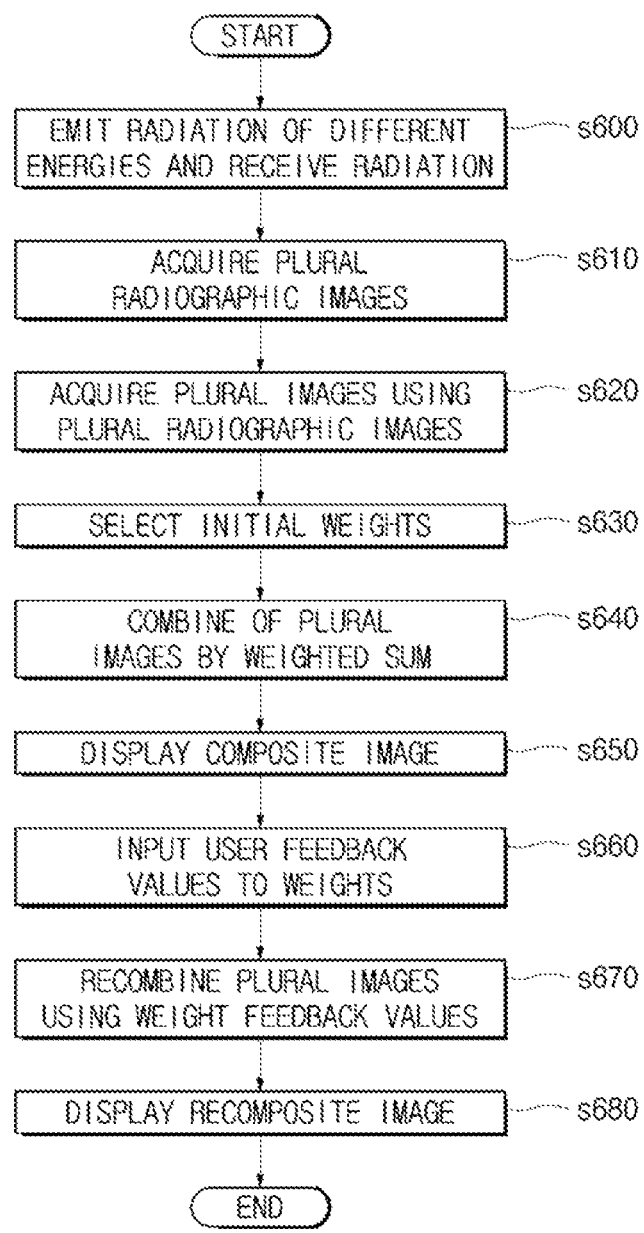
FIG. 13 is a flowchart illustrating a control method of a radiographic imaging apparatus in accordance with an exemplary embodiment.

FIG. 13 is a flowchart illustrating a control method of a radiographic imaging apparatus in accordance with an exemplary embodiment.

As shown in FIG. 13, in the control method of the radiographic imaging apparatus in accordance with this embodiment, different tube voltages are sequentially applied to the radiation tube of the radiation source and thus, radiation of different energy bands is sequentially emitted to an object. The radiation detector may generate and output radioactive signals by receiving the radiation of different energy bands emitted to the object and transmitted by the object (Operation S600).

Thereafter, a plurality of radiographic images corresponding to the emitted radiation of different energy bands is acquired by reading the generated and output radioactive signals (Operation S610). Such acquired radiographic images may be used as basic images.

A plurality of deformed images is acquired using the acquired plural radiographic images. The plural acquired deformed images may be different images. The plural acquired deformed images may include a tissue emphasized image in which tissues are emphasized and a contrast enhanced image in which contrast is enhanced (Operation S620).

Thereafter, at least one initial weight applied to each of the images is selected (Operation S630). The initial weight may be determined according to predefined system settings. The predefined system settings may be defined by a user or a system designer.

The selected initial weight is applied to each image, and then the plural images are combined by weighted sum (Operation S640).

A composite image acquired by combining the plural images may be displayed to the user through the user interface (Operation S650).

The user may confirm the composite image displayed through the user interface, and input at least one weight of the composite image through the user interface so as to input user feedback values of the composite image (Operation S660).

The radiographic imaging apparatus may recombine the plural images using the weight input through the user interface according to user feedback values (Operation S670).

A recombined image may be also displayed through the user interface (Operation S680).

As is apparent from the above description, a radiographic imaging apparatus and a control method thereof in accordance with an exemplary embodiment may combine different radiographic images according to a user request and display an acquired composite image to a user.

In the radiographic imaging apparatus, a contrast enhanced image and a tissue emphasized image are combined as needed by the user and thus, the user may properly confirm structures, tissues, and lesions within an object.

Further, if the radiographic imaging apparatus is used as a diagnostic radiographic imaging apparatus, a user, such as a doctor, may make a proper diagnosis of a diseased region.

Further, proper weights may be applied to radiographic images of multiple energy bands as needed by a user and then the respective radiographic images may be combined. Therefore, the structures, tissues, and lesions within the object may be more easily and correctly confirmed.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A radiographic imaging apparatus comprising:
   a display; and
   a processor configured to:
      combine a plurality of images comprising a contrast enhanced image and a tissue emphasized image by applying corresponding first weights to the contrast enhanced image and the tissue emphasized image, respectively,
      control the display to display a track and a display mark on the track, the display mark corresponding to the first weights, and
      control the display to display the contrast enhanced image when the display mark is located at an end of the track and to display the tissue emphasized image when the display mark is located at another end of the track,
   wherein the processor is further configured to control the display to display second weights and a composite image which is generated, by the processor, by applying corresponding second weights to the contrast enhanced image and the tissue emphasized image, respectively, wherein the second weight and the first weight that are applied to the contrast enhanced image are different from one another, and wherein the second weight and the first weight that are applied to the tissue emphasized image are different from one another,
   wherein, in response to receiving an input for locating the display mark at a center of the track, the processor is further configured to control the display to display the composite image which is generated, by the processor, by the processor is further configured to control the display to display the composite image which is generated, by the processor, by:
      applying the second weights of a same value to each of the contrast enhanced image and the tissue emphasized image, and
      combining together the contrast enhanced image and the tissue emphasized image to which the second weights have been applied.

2. The radiographic imaging apparatus according to claim 1, wherein the processor acquires a basic image of an object, and acquires the contrast enhanced image and the tissue emphasized image using the basic image.

3. The radiographic imaging apparatus according to claim 2, wherein the basic image includes a plurality of radiographic images of different energy bands.

4. The radiographic imaging apparatus according to claim 1, wherein the display comprises a touchscreen.

5. A control method of a radiographic imaging apparatus comprising:
   obtaining a plurality of images comprising a contrast enhanced image and a tissue emphasized image;
   combining the contrast enhanced image and the tissue emphasized image by applying first weights to the contrast enhanced image and the tissue emphasized image, respectively;
   displaying a combined image corresponding to the first weights;
   displaying an adjustment bar comprising a track and a display mark, wherein the first weights applied to the contrast enhanced image and the tissue emphasized image correspond to a location of the display mark, the contrast enhanced image is displayed if the display mark is located at an end of the track, and the tissue emphasized image is displayed if the display mark is located at another end of the track;
   additionally receiving a user input of second weights, which are different from the first weights, based on a changed location of the display mark;
   combining the contrast enhanced image and the tissue emphasized image by applying corresponding second weights to the contrast enhanced image and the tissue emphasized image, to obtain the combined image corresponding to the second weights; and
   displaying the second weights and the combined image corresponding to the second weights,
   wherein the displaying the combined image corresponding to the first weights comprises:
   displaying a composite image which is generated by applying the first weights of a same value to each of the contrast enhanced image and the tissue emphasized image when the display mark is located at a center of the track, and combining together the contrast enhanced image and the tissue emphasized image to which the first weights have been applied.

6. The control method according to claim 5, further comprising:
   acquiring a basic image of an object; and
   acquiring the contrast enhanced image and the tissue emphasized image, using the basic image.

7. The control method according to claim 6, wherein the acquiring the basic image comprises:
   acquiring the basic image by emitting radiation of different energy bands to the object and receiving radiation of different energy bands transmitted by the object.

* * * * *